United States Patent
Yang et al.

(10) Patent No.: US 11,707,487 B2
(45) Date of Patent: Jul. 25, 2023

(54) EPCAM ANTIBODY AND CAR-T CELLS

(71) Applicant: Affyimmune Therapeutics, Inc., Natick, MA (US)

(72) Inventors: Huan Yang, Millbury, MA (US); Moonsoo Jin, New York, NY (US); Janusz Puc, Sudbury, MA (US)

(73) Assignee: AffyImmune Therapeutics, Inc., Natick, MA (US)

(*) Notice: Subject to any disclaimer, the term of this patent is extended or adjusted under 35 U.S.C. 154(b) by 148 days.

(21) Appl. No.: 17/228,844

(22) Filed: Apr. 13, 2021

(65) Prior Publication Data

US 2021/0317229 A1    Oct. 14, 2021

Related U.S. Application Data

(60) Provisional application No. 63/009,018, filed on Apr. 13, 2020.

(51) Int. Cl.

| | | |
|---|---|---|
| *A61K 35/17* | (2015.01) | |
| *C07K 16/30* | (2006.01) | |
| *C07K 14/725* | (2006.01) | |
| *A61P 35/00* | (2006.01) | |
| *A61K 39/00* | (2006.01) | |
| *C12N 5/10* | (2006.01) | |
| *C07K 16/46* | (2006.01) | |
| *C07K 14/705* | (2006.01) | |

(52) U.S. Cl.
CPC ...... *A61K 35/17* (2013.01); *A61K 39/001166* (2018.08); *A61P 35/00* (2018.01); *C07K 14/7051* (2013.01); *C07K 16/30* (2013.01); *C07K 16/46* (2013.01); *C12N 5/10* (2013.01); *C07K 14/70517* (2013.01); *C07K 14/70521* (2013.01); *C07K 2317/565* (2013.01); *C07K 2317/622* (2013.01); *C07K 2317/73* (2013.01); *C07K 2319/03* (2013.01)

(58) Field of Classification Search
CPC . A61K 35/17; A61K 39/001166; A61P 35/00; C07K 14/7051; C07K 16/30; C07K 16/46; C07K 14/70517; C07K 14/70521; C07K 2317/565; C07K 2317/622; C07K 2317/73; C07K 2319/03; C12N 5/10
USPC .......... 424/93.2; 530/387.3, 388.22; 435/328
See application file for complete search history.

(56) References Cited

U.S. PATENT DOCUMENTS

| | | |
|---|---|---|
| 7,777,010 B2 | 8/2010 | Logtenberg |
| 2007/0054362 A1 | 3/2007 | Van Berkel et al. |
| 2007/0128183 A1 | 6/2007 | Meinke et al. |

OTHER PUBLICATIONS

Sela-Culang, I., Kunik, V., & Ofran, Y. (2013). The structural basis of antibody-antigen recognition. Frontiers in immunology, 4, 302. (Year: 2013).*
Vajdos, F. F., Adams, C. W., Breece, T. N., Presta, L. G., De Vos, A. M., & Sidhu, S. S. (2002). Comprehensive functional maps of the antigen-binding site of an anti-ErbB2 antibody obtained with shotgun scanning mutagenesis. Journal of molecular biology, 320(2), 415-428. (Year: 2002).*
Chen, C., Roberts, V. A., & Rittenberg, M. B. (1992). Generation and analysis of random point mutations in an antibody CDR2 sequence: many mutated antibodies lose their ability to bind antigen. The Journal of experimental medicine, 176(3), 855-866. (Year: 1992).*
International Search Report and Written Opinion for PCT/2021/26980, dated Oct. 15, 2021, 11 pages.
Ang et al. "Intraperitoneal immunotherapy with T cells stably and transiently expressing anti-EpCAM CAR in xenograft models of peritoneal carcinomatosis," Oncotarget, 2017, vol. 8, (No. 8), pp. 13545-13559.

* cited by examiner

*Primary Examiner* — Anne Marie S Wehbe
*Assistant Examiner* — Brendan Thomas Tinsley
(74) *Attorney, Agent, or Firm* — Perkins Coie LLP; Viola Kung

(57) ABSTRACT

The present invention provides EpCAM antibodies with different affinities. The present invention also provides chimeric antigen receptors (CARs) specific to EpCAM. CAR T cells comprising human EpCAM scFv having a low and sufficient affinity to EpCAM can avoid targeting healthy tissues with low EpCAM expression while exhibiting long-term efficacy against tumor tissues with high EpCAM expression. The present invention also relates to an adoptive cell therapy method for treating cancer by administering the CAR-T cells comprising human EpCAM scFv to a subject suffering from cancer, whereby the CAR T cells bind to the cancer cells overexpressing EpCAM and kill the cancer cells.

13 Claims, 7 Drawing Sheets

Specification includes a Sequence Listing.

|  | FR1 | CDR1 | FR2 | CDR2 |
|---|---|---|---|---|
| UBS-54 VH: | QVQLVQSGAEVKKPGSSVRVSCKAS | GGTFSSY | AISWVRQAPGQGLEWMGGI | IPIFGT |

ANYAQKFQGRVTITADESTSTAYMELSSLRSEDTAVYYCAR DPFLHY WGQGTLVT

FR3                        CDR3      FR4

UBS-54 CDR-H3:   DPFLHY
D1A CDR-H3:   APFLHY
F3A CDR-H3:   DPALHY
L4A CDR-H3:   DPFAHY
Y6A CDR-H3:   DPFLHA

UBS-54 CDR-H3: DPFLHY
Y6A CDR-H3: DPFLHA
Y6V CDR-H3: DPFLHV
Y6L CDR-H3: DPFLHL
Y6F CDR-H3: DPFLHF

SEQUENCE LISTING

<160> NUMBER OF SEQ ID NOS: 23

<210> SEQ ID NO 1
<211> LENGTH: 112
<212> TYPE: PRT
<213> ORGANISM: Homo sapiens

<400> SEQUENCE: 1

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Phe Leu His Tyr Trp Gly Gln Gly Thr Leu Val Thr
            100                 105                 110

<210> SEQ ID NO 2
<211> LENGTH: 6
<212> TYPE: PRT
<213> ORGANISM: Artificial Sequence
<220> FEATURE:
<223> OTHER INFORMATION: Synthetic

<400> SEQUENCE: 2

Asp Pro Phe Leu His Tyr
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Ala Pro Phe Leu His Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

Asp Pro Ala Leu His Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

```
Asp Pro Phe Ala His Tyr
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

Asp Pro Phe Leu His Ala
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic

<400> SEQUENCE: 7

Asp Pro Phe Leu His Leu
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Asp Pro Phe Leu His Val
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic

<400> SEQUENCE: 9

Asp Pro Phe Leu His Phe
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Gly Gly Thr Phe Ser Ser Tyr
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic

<400> SEQUENCE: 11
```

```
Ile Pro Ile Phe Gly Thr
1               5

<210> SEQ ID NO 12
<211> LENGTH: 16
<212> TYPE: PRT
<213> ORGANISM: Artificial Sequence
<220> FEATURE:
<223> OTHER INFORMATION: Synthetic

<400> SEQUENCE: 12

Arg Ser Ser Gln Ser Leu Leu His Ser Asn Gly Tyr Asn Tyr Leu Asp
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: Synthetic

<400> SEQUENCE: 13

Leu Gly Ser Asn Arg Ala Ser
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic

<400> SEQUENCE: 14

Met Gln Ala Leu Gln Thr Phe Thr
1               5

<210> SEQ ID NO 15
<211> LENGTH: 110
<212> TYPE: PRT
<213> ORGANISM: Homo sapiens

<400> SEQUENCE: 15

Glu Ile Glu Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Phe Thr Phe Gly Pro Gly Thr Lys Val Glu Ile
            100                 105                 110

<210> SEQ ID NO 16
<211> LENGTH: 111
<212> TYPE: PRT
<213> ORGANISM: Homo sapiens

<400> SEQUENCE: 16
```

Glu Ile Glu Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Phe Thr Phe Gly Pro Gly Thr Lys Val Glu Ile Lys
            100                 105                 110

<210> SEQ ID NO 17
<211> LENGTH: 112
<212> TYPE: PRT
<213> ORGANISM: Homo sapiens

<400> SEQUENCE: 17

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Phe Leu His Ala Trp Gly Gln Gly Thr Leu Val Thr
            100                 105                 110

<210> SEQ ID NO 18
<211> LENGTH: 112
<212> TYPE: PRT
<213> ORGANISM: Homo sapiens

<400> SEQUENCE: 18

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Phe Leu His Leu Trp Gly Gln Gly Thr Leu Val Thr
            100                 105                 110

<210> SEQ ID NO 19
<211> LENGTH: 112
<212> TYPE: PRT
<213> ORGANISM: Homo sapiens

<400> SEQUENCE: 19

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Phe Leu His Val Trp Gly Gln Gly Thr Leu Val Thr
            100                 105                 110

<210> SEQ ID NO 20
<211> LENGTH: 112
<212> TYPE: PRT
<213> ORGANISM: Homo sapiens

<400> SEQUENCE: 20

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Phe Leu His Tyr Trp Gly Gln Gly Thr Leu Val Thr
            100                 105                 110

<210> SEQ ID NO 21
<211> LENGTH: 112
<212> TYPE: PRT
<213> ORGANISM: Homo sapiens

<400> SEQUENCE: 21

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr

```
                    65                   70                   75                   80
Met Glu Leu Ser Ser Leu Arg Ser Glu Asp Thr Ala Val Tyr Tyr Cys
                        85                   90                   95

Ala Arg Asp Pro Phe Ala His Tyr Trp Gly Gln Gly Thr Leu Val Thr
                    100                  105                  110

<210> SEQ ID NO 22
<211> LENGTH: 112
<212> TYPE: PRT
<213> ORGANISM: Homo sapiens

<400> SEQUENCE: 22

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                    85                   90                  95

Ala Arg Asp Pro Phe Leu His Phe Trp Gly Gln Gly Thr Leu Val Thr
                100                  105                  110

<210> SEQ ID NO 23
<211> LENGTH: 15
<212> TYPE: PRT
<213> ORGANISM: Artificial Sequence
<220> FEATURE:
<223> OTHER INFORMATION: Synthetic

<400> SEQUENCE: 23

Gly Gly Gly Gly Ser Gly Gly Gly Gly Ser Gly Gly Gly Gly Ser
1               5                   10                  15
```

EPCAM ANTIBODY AND CAR-T CELLS

This application claims priority to U.S. Provisional Application No. 63/009,018, filed Apr. 13, 2020; the contents of which is incorporated herein by reference in its entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Apr. 12, 2021 and a size of 11.5 kilobytes. The Sequence Listing filed via EFS-Web is part of the specification and is hereby incorporated in its entirety by reference herein.

FIELD OF THE INVENTION

The present invention relates to EpCAM antibody and EpCAM-CAR-T Cells, which are useful in the field of adoptive immunity gene therapy for tumors. The invention particularly relates to chimeric antigen receptors comprising EpCAM single-chain variable fragment having functionally sufficient but low affinities to EpCAM, which mitigate cytotoxicity to normal tissues.

BACKGROUND OF THE INVENTION

Immunotherapy is emerging as a highly promising approach for the treatment of cancer. Genetically modifying T cells with CARs is a common approach to design tumor-specific T cells. CAR (chimeric antigen receptor)-T cells targeting tumor-associated antigens can be infused into patients (adoptive cell transfer or ACT) representing an efficient immunotherapy approach. The advantage of CAR-T technology compared with chemotherapy or antibody is that reprogrammed engineered T cells can proliferate and persist in the patient and work like a living drug.

CAR molecules are composed of synthetic binding moieties, typically an antibody-derived single chain fragment variable (scFv) or any native antigen-sensing element, fused to intracellular signaling domains composed of the TCR zeta chain and costimulatory molecules such as CD28 and/or 4-1BB[1, 2]. The advantages of CAR mediated targeting include: 1) the provision of activation, proliferation, and survival signals in-cis via a single binding event, compared to the natural, non-integrated TCR and costimulatory signaling; 2) the ability to bypass the downregulation of MHC by tumor cells through MHC-independent antigen recognition; and 3) a reduced activation threshold as well as recognition of tumor cells with low antigen density enabled by the high affinity interaction between CAR and antigen[3, 4].

The ideal CAR target antigen would be a native, surface-exposed tumor neoantigen that is highly expressed in tumor tissues and is undetectable in healthy tissues. However, due to the implicit rarity of such antigens, many commonly targeted solid tumor antigens, are also expressed by non-tumor tissues, albeit at lower levels. CAR molecules with high affinity to such antigens can lead to collateral targeting of healthy tissues resulting in on-target, off-tumor toxicity, a major limiting factor to the progress of CAR T cell therapy to date.

Conventional CARs are constructed using a single-chain antibody format, and are selectively engineered to possess sub- to low nanomolar affinities for target antigens. However, increased CAR T cell sensitivity may be an advantage only when targeting true tumor antigens or those with the highest levels of restriction. Otherwise, increased sensitivity comes at the price of reduced selectivity with lysis of target-expressing cells in a manner largely insensitive to antigen density.

EpCAM (Epithelial Cell Adhesion Molecule) (CD326) antigen is a 39-40 kDa cell surface glycoprotein that is encoded by EpCAM gene. EpCAM plays a crucial role in cell adhesion, growth, proliferation, inflammation, cancer and metastasis. EpCAM is highly overexpressed in many types of tumors such as breast cancer, ovarian cancer, non-small cell lung cancer, pancreas cancer, stomach cancer, colon cancer and colorectal cancer. EpCAM is also expressed in many normal tissues but its expression in tumor tissues is significantly higher.

The use of T cells to fight cancer is dependent upon optimally activated T cells, whether they are endogenous or genetically engineered. Continuous exposure of T cells to antigen results in their exhaustion, a state characterized by the deterioration of cellular functions. Exhausted T cells display loss of effector functions, begin to express multiple inhibitory proteins and are defined by an altered transcriptional repertoire.

High affinity EpCAM CAR-T cells recognize epithelial cell adhesion molecule-expressing cells: both normal epithelial tissues with low levels of EpCAM, and carcinomas expressing it at considerably higher levels. The recognition of antigen both on normal, non-target cells as well as on cancer cells can lead to both unwanted toxicity and T cell exhaustion.

There exists a need for CARs with improved therapeutic index, i.e., CARs that can kill tumor while minimizing systemic toxicity.

BRIEF DESCRIPTION OF THE DRAWINGS

FIG. 1A also shows the CDR-H3 of UBS-54 (SEQ ID NO: 2) and CDR-H3 of four variants with alanine substitution in CDR-H3. D1A: SEQ ID NO: 3. F3A: SEQ ID NO: 4. L4A: SEQ ID NO: 5, Y6A: SEQ ID NO: 6.

DETAILED DESCRIPTION OF THE INVENTION

Definitions

Figures 1A, 1B:
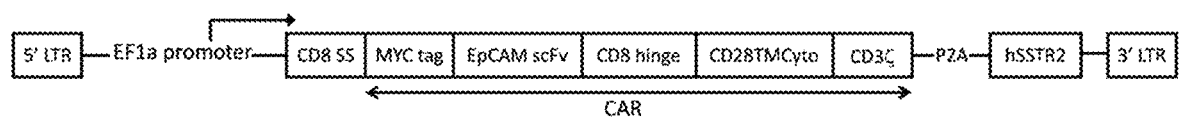
FIG. 1A shows the variable regions of the heavy chain ($V_H$, SEQ ID NO: 1) of UBS-54 huMab.
FIG. 1B shows the schematic demonstration of the EpCAM targeting CAR construct. The scFv component is the sequence from UBS-54 huMab or one of the alanine substitution variants (D1A, F3A, L4A, and Y6A). LTR=long terminal repeat; SS=signal sequence; scFv=single-chain variable fragment; TMCyto=transmembrane and cytosolic domain.

As used herein, "about" refers to ±10% of the recited value.

As used herein, "adoptive T cell therapy" involves the isolation and ex vivo expansion of tumor specific T cells to achieve greater number of T cells than what could be obtained by vaccination alone. The tumor specific T cells are then infused into patients with cancer in an attempt to give their immune system the ability to overwhelm remaining tumor via T cells which can attack and kill cancer.

As used herein, "affinity" is the strength of binding of an antibody (e.g., EpCAM antibody) to its antigen (e.g., EpCAM). Affinity is typically measured and reported by the equilibrium dissociation constant ($K_D$ or Kd), which is used to evaluate and rank order strengths of bimolecular interactions.

As used herein, a "chimeric antigen receptor (CAR)" means a fused protein comprising an extracellular domain capable of binding to an antigen, a hinge domain, a transmembrane domain, and at least one intracellular domain. The receptor is chimeric because they combine both antigen-binding and T-cell activating functions into a single receptor. The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell.

As used herein, a "domain" means one region in a polypeptide which is folded into a particular structure independently of other regions.

As used herein, a "single chain variable fragment (scFv)" means a single chain polypeptide derived from an antibody which retains the ability to bind to an antigen. An example of the scFv includes an antibody polypeptide which is formed by a recombinant DNA technique and in which Fv regions of immunoglobulin heavy chain fragment ($V_H$ domain) and light chain fragment ($V_L$ domain) are linked via a spacer sequence. Various methods for engineering an scFv are known to a person skilled in the art. scFv can be in a format of $V_H$-linker-$V_L$ or $V_L$-linker-$V_H$. The linker can be 2-30 amino acids, preferably 5-20 amino acids.

As used herein, a "tumor antigen" means a biological molecule present in tumor and having antigenicity.

Description

Chimeric antigen receptor (CAR)-T cell therapy has shown robust anti-cancer responses in hematologic malignancies. However, application of CAR-T cell therapeutic approach to solid tumors has been hindered by multiple challenges, one of which is on-target/off-tumor cytotoxicity to normal tissues. Tumor-specific antigens exclusively present on tumor cells are rare. Most CAR-T cells are designed to target tumor associated antigens (TAAs) expressed in high levels on tumor cells. Yet, normal tissues express these antigens as well, albeit at much lower densities.

Epithelial cell adhesion molecule (EpCAM) is highly expressed in epithelial cells and overexpressed in tumor cells in a variety of epithelial carcinomas. High-affinity (nM range) EpCAM-targeting CAR-T cells kill both normal human epithelial cells and EpCAM-high tumor cells in vitro. To mitigate the on-target/off-tumor cytotoxicity, the inventors developed a strategy for fine tuning the affinity of CARs to selectively target tumor cells.

Huls, et al (Nat Biotechnol. 17, 276-281 (1999)) isolated a huMab UBS-54 (UBS-54) that was specific for EpCAM with an affinity of 5 nM. The $V_H$ and $V_L$ sequences of UBS-54 are shown in U.S. Pat. No. 7,777,010, and are incorporated herein by reference. The inventors selected CDR3-$V_H$ of UBS-54 for engineering antibodies with different affinities to EpCAM because CDR3 of $V_H$ occupies a centric position in the antigen binding surface and has the most diversity.

The present invention provides anti-EpCAM antibodies with different affinities to EpCAM. Because the heavy chain variable CDR3 region (CDR-H3) occupies a centric position in the antigen binding surface and has the most diversity[2], the inventors have engineered CDR-H3 for affinity tuning.

The present invention is directed to an antibody or its antigen-binding fragment that binds to EpCAM, wherein the CDR-H3 has the amino acid sequence DPFLHA (SEQ ID NO: 6), DPFLHL (SEQ ID NO: 7), DPFLHV(SEQ ID NO: 8), APFLHY(SEQ ID NO: 3), DPFAHY(SEQ ID NO: 5), or DPFLHF(SEQ ID NO: 9).

In one embodiment, the heavy chain variable CDR1 of the antibody or its antigen-binding fragment has the sequence of GGTFSSY (SEQ ID NO: 10) and the heavy chain variable CDR2 has the sequence of IPIFGT (SEQ ID NO: 11).

In one embodiment, the light chain variable CDR1 of the antibody or its antigen-binding fragment has the sequence of RSSQSLLHSNGYNYLD (SEQ ID NO: 12), the light chain variable CDR2 has the sequence of LGSNRAS (SEQ ID NO: 13), and the light chain variable CDR3 has the sequence of MQALQTFT (SEQ ID NO: 14).

In one embodiment, the light chain variable domain ($V_L$) of the antibody or its antigen-binding fragment has the amino acid sequence of SEQ ID NO: 15 or 16.

In one embodiment, the antibody or its antigen-binding fragment has the same $V_H$ frames as those of UBS-54 (see FIG. 1).

In one embodiment, the antibody or its antigen-binding fragment has the same $V_L$ frames as those of UBS-54 (SEQ ID NO: 15).

In one preferred embodiment, the antibody or its antigen-binding fragment has the same $V_H$ frames and $V_L$ frames as those of UBS-54.

In one preferred embodiment, the antibody or its antigen-binding fragment has the same $V_H$ sequence as those of UBS-54, except CDR-H3 has one amino acid variation and has the amino acid sequence of DPFLHA, i.e., $V_H$ has the amino acid sequence of SEQ ID NO: 17.

In one preferred embodiment, the antibody or its antigen-binding fragment has the same $V_H$ sequence as those of UBS-54, except CDR-H3 has one amino acid variation and has the amino acid sequence of DPFLHL, i.e., $V_H$ has the amino acid sequence of SEQ ID NO: 18.

In one preferred embodiment, the antibody or its antigen-binding fragment has the same $V_H$ sequence as those of UBS-54, except CDR-H3 has one amino acid variation and has the amino acid sequence of DPFLHV, i.e., $V_H$ has the amino acid sequence of SEQ ID NO: 19.

In one preferred embodiment, the antibody or its antigen-binding fragment has the same $V_H$ sequence as those of UBS-54, except CDR-H3 has one amino acid variation and has the amino acid sequence of APFLHY, i.e., $V_H$ has the amino acid sequence of SEQ ID NO: 20.

In one preferred embodiment, the antibody or its antigen-binding fragment has the same $V_H$ sequence as those of UBS-54, except CDR-H3 has one amino acid variation and has the amino acid sequence of DPFAHY, i.e., $V_H$ has the amino acid sequence of SEQ ID NO: 21.

In one preferred embodiment, the antibody or its antigen-binding fragment has the same $V_H$ and $V_L$ sequences as those of UBS-54, except CDR-H3 has one amino acid variation and has the amino acid sequence of DPFLHF, i.e., $V_H$ has the amino acid sequence of SEQ ID NO: 22.

The present invention provides chimeric antigen receptors targeting EpCAM, using the affinity-tuned anti-EpCAM antibody. The inventor has constructed a panel of affinity-variant CARs that comprise affinity-tuned human anti-EpCAM scFv. CAR T cells comprising anti-EpCAM scFv having micromolar affinity targeting EpCAM have improved efficacy and safety over conventional CARs, as they are capable of lysing cells overexpressing target antigens while sparing normal cells with much lower densities.

The present invention is directed to a chimeric antigen receptor fusion protein (CAR) comprising from N-terminus to C-terminus: (i) a low affinity anti-EpCAM scFv, (ii) a hinge domain, (iii) a transmembrane domain, (iv) at least one co-stimulatory domains, and (v) an activating domain.

In one embodiment, the CAR comprises a low affinity anti-EpCAM scFv comprising the heavy chain variable CDR3 region with the amino acid sequence DPFLHA, DPFLHL, or DPFLHV. The scFv may further comprise the heavy chain variable CDR1 of the amino acid sequence of GGTFSSY and the heavy chain variable CDR2 of the amino acid sequence of IPIFGT. The scFv may further comprise light chain variable CDR1 of the amino acid sequence of RSSQSLLHSNGYNYLD, the light chain variable CDR2 of the amino acid sequence of LGSNRAS, and the light chain variable CDR3 of the amino acid sequence of MQALQTFT.

In one embodiment, the low affinity anti-EpCAM scFv is identical to that of UBS-54 except the CDR-H3 has the amino acid sequence of DPFLHA, DPFLHL, or DPFLHV.

The CAR of the present invention comprises a spacer sequence as a hinge to connect scFv with the transmembrane domain and spatially separate antigen binding domain from the endodomain. A flexible spacer allows to the binding domain to orient in different directions to enable its binding to a tumor antigen. The spacer sequence may, for example, comprise an IgG1 Fc region, an IgG1 hinge or a CD8 stalk, or a combination thereof. A human CD28 or CD8 stalk is preferred.

The CAR of the present invention comprises a transmembrane domain which spans the membrane. The transmembrane domain may be derived from a natural polypeptide, or may be artificially designed. The transmembrane domain derived from a natural polypeptide can be obtained from any membrane-binding or transmembrane protein. For example, a transmembrane domain of a T cell receptor α or β chain, a CD3 zeta chain, CD28, CD3-epsilon, CD45, CD4, CD5, CD8, CD9, CD16, CD22, CD33, CD37, CD64, CD80, CD86, CD134, CD137, ICOS, CD154, or a GITR can be used. The artificially designed transmembrane domain is a polypeptide mainly comprising hydrophobic residues such as leucine and valine. In preferred embodiments, the transmembrane domain is derived from CD28 or CD8, which give good receptor stability.

The CAR of the present invention comprises one or more co-stimulatory domains selected from the group consisting of human CD28, 4-1BB (CD137), ICOS-1, CD27, OX 40 (CD137), DAP10, and GITR (AITR). In one embodiment, the CAR comprises one co-stimulating domain of CD28.

The endodomain (the activating domain) is the signal-transmission portion of the CAR. After antigen recognition, receptors cluster and a signal is transmitted to the cell. The most commonly used endodomain component is that of CD3-zeta (CD3 Z or CD3ζ), which contains 3 immunoreceptor tyrosine-based activation motifs (ITAM). This transmits an activation signal to the T cell after antigen is bound. CD3-zeta may not provide a fully competent activation signal and additional co-stimulatory signaling may be needed. For example, one or more co-stimulating domains can be used with CD3-Zeta to transmit a proliferative/survival signal.

The CAR of the present invention may comprise a signal peptide N-terminal to EpCAM scFv so that when the CAR is expressed inside a cell, such as a T-cell, the nascent protein is directed to the endoplasmic reticulum and subsequently to the cell surface, where it is expressed. The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases. As an example, the signal peptide may derive from human CD8 or GM-CSF, or a variant thereof having 1 or 2 amino acid mutations provided that the signal peptide still functions to cause cell surface expression of the CAR.

The present invention provides a nucleic acid encoding the CAR described above. The nucleic acid encoding the CAR can be prepared from an amino acid sequence of the specified CAR by a conventional method. A base sequence encoding an amino acid sequence can be obtained from the aforementioned NCBI RefSeq IDs or accession numbers of GenBenk for an amino acid sequence of each domain, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

The nucleic acid encoding the CAR of the present invention can be inserted into a vector, and the vector can be introduced into a cell. For example, a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a Sendai virus vector, an Epstein-Barr virus (EBV) vector, and a HSV vector can be used. As the virus vector, a virus vector lacking the replicating ability so as not to self-replicate in an infected cell is preferably used.

For example, when a retrovirus vector is used, the process of the present invention can be carried out by selecting a suitable packaging cell based on a LTR sequence and a packaging signal sequence possessed by the vector and preparing a retrovirus particle using the packaging cell. Examples of the packaging cell include PG13 (ATCC CRL-10686), PA317 (ATCC CRL-9078), GP+E-86 and GP+en-vAm-12, and Psi-Crip. A retrovirus particle can also be prepared using a 293 cell or a 293T cell having high transfection efficiency. Many kinds of retrovirus vectors produced based on retroviruses and packaging cells that can be used for packaging of the retrovirus vectors are widely commercially available from many companies.

The present invention provides T cells or natural killer cells (NK cells) modified to express the CAR as described above. CAR-T cells or CAR-NK cells of the present invention bind to EpCAM via the anti-EpCAM scFv of CAR, thereby a signal is transmitted into the cell, and as a result, the cell is activated. The activation of the cell expressing the CAR is varied depending on the kind of a host cell and an intracellular domain of the CAR, and can be confirmed based on, for example, release of a cytokine, improvement of a cell proliferation rate, change in a cell surface molecule, killing target cells, or the like as an index.

T cells or NK cells modified to express the EpCAM-CAR can be used as a therapeutic agent for a disease. The therapeutic agent comprises the T cells expressing the EpCAM-CAR as an active ingredient, and may further comprise a suitable excipient. Examples of the excipient include pharmaceutically acceptable excipients known to a person skilled in the art.

The present invention further provides an adoptive cell therapy method for treating cancer. The method comprises the steps of: administering the CAR-T cells or CAR-NK cells of the present invention to a subject suffering from cancer, wherein the cancer cells of the subject overexpress EpCAM, and the CAR-T cells or CAR-NK cells bind to cancer cells to kill the cancer cells. "Overexpress", as used herein, refers to cancer cells have surface expression of EpCAM significantly higher than that of normal cells. Cancers suitable to be treated by the present invention include, but not limited to colon, intestine, breast, lung, prostate, gastric, pancreas, bladder, gall bladder, nasopharyngeal, colorectal, ovarian, and lung cancer.

The present invention demonstrates that T cells expressing affinity-tuned CAR variants against EpCAM spared normal tissues expressing modest amounts of EpCAM while being effective in eliminating EpCAM-rich cancer cell lines in vitro, and effective in regressing tumor and prolonging survival in an in vivo xenografts mouse model. CAR T cells equipped with low-affinity scFvs showed antigen-dependent activation, proliferation, and Th1-like cytokine secretion when co-cultured with target cells expressing varied levels of EpCAM.

CARs possessing low affinity anti-EpCAM antibody (in scFv format) in the 50 nM to 50 μM range minimize off-tumor toxicity against basally expressed antigens in normal tissues, and also increases therapeutic index, in comparison with CARs having higher affinities. CAR T cells with target affinities in the micromolar range can avoid targeting healthy tissue with basal antigen expression while simultaneously exhibiting comparable potency and long-term efficacy against tumor tissue with high target expression. The micromolar affinity CAR enables T cells to neglect normal tissues having low EpCAM expression. High affinity and avidity interactions by nanomolar affinity EpCAM-CAR can reduce T cells' propensity for serial killing, potentially causing exhaustion or increased susceptibility to activation-induced cell death.

The following examples further illustrate the present invention. These examples are intended merely to be illustrative of the present invention and are not to be construed as being limiting.

EXAMPLES

Materials and Methods

Example 1

Preparing EpCAM Antibodies Having Different CDR3 of $V_H$

The $V_H$ and $V_L$ sequences of UBS-54 were shown in U.S. Pat. No. 7,777,010. An oligopeptide linker of GGGGS GGGGS GGGGS (SEQ ID NO: 23) was used to connect two sequences to generate the full sequence of scFv in the $V_H$-linker-$V_L$ orientation. The DNA sequence of UBS-54 scFv was derived from the amino acid sequences by reverse translation. A DNA fragment encoding UBS-54 scFv was synthesized and cloned into a pcDNA3.1 based scFv-Fc recombinant protein expression plasmid. To produce recombinant scFv-Fc protein, HEK293T cells were transfected with the expression plasmid using 293Fectin™. Supernatant was collected after 72 hrs and cleared by centrifugation and filtration. scFv-Fc protein was purified by protein A affinity chromatography from the supernatant. Protein expression plasmids for EpCAM scFv variants were generated by genetic engineering and molecular cloning. A BlpI and SbfI fragment of UBS-54 expression plasmid was replaced with a DNA fragment encoding each CDR-H3 variant to generate the corresponding scFv-Fc expression plasmid. EpCAM scFv-Fc proteins were purified as previously mentioned.

Example 2

Cell Lines and Primary Human Lymphocytes

Human colorectal adenocarcinoma HT-29 cells (ATCC) were cultured in McCoy's 5a (Gibco) containing 10% FBS (Gibco). Human gastric cancer MKN-28 cells and human pancreatic adenocarcinoma Capan2 cells (ATCC) were cultured in RPMI-1640 (Gibco) containing 10% FBS (Gibco). Human breast cancer MDA-MB-231 cells (ATCC) and human embryonic kidney HEK293T cells (ATCC) were cultured in DMEM with high glucose and GlutaMAX (Gibco) containing 10% FBS (Gibco). Human normal primary epithelial cells (Cell Biologics Inc.) were cultured in complete human epithelial cell medium kit (Cell Biologics Inc.). HT-29, MKN-28, Capan-2, MDA-MB-231 and HEK293T cells were transduced with lentivirus encoding Firefly Luciferase-F2A-GFP (Biosettia) for luminescence-based Effector to Target assay. All cells were incubated at 37° C. in a 5% $CO_2$ humidified incubator.

Human primary T lymphocytes were sorted from leukopaks (Allcells Inc.) using CD4&CD8 microbeads (Miltenyi Biotec) and cultured in TexMACS (Miltenyi Biotec) supplemented with 5% human AB serum (Sigma), 12.5 ng/ml IL-7 and 12.5 ng/ml IL-15 (Miltenyi Biotec). T cells were incubated at 37° C. in a 5% $CO_2$ humidified incubator.

Example 3

Construction of EpCAM Targeting CAR Constructs

UBS-54 scFv consisted of $V_H$ and $V_L$ sequences from UBS-54 huMab (U.S. Pat. No. 7,777,010). A 15 amino acid linker of SEQ ID NO: 22 was used to connect two sequences. CDR-H3 sequences were modified to generate scFv variants. scFv sequences were synthesized and cloned into a lentiviral backbone (Genscript). UBS-54 scFv and variants were fused at the C-terminus directly to the CD8 hinge, CD28 transmembrane and cytoplasmic domains, and CD3z cytoplasmic domain. A reporter gene for CAR T cell imagine, SSTR2, was linked to CAR at the C-terminus using a 'ribosome skipping' porcine teschovirus-1 2A (P2A) sequence. The EpCAM CAR construct is shown in FIG. 1B. The complete CAR inserts were then subcloned into a pLenti backbone (Vedvyas Y, et al. JCI Insight 1, e90064) (2016).

Example 4

Lentivirus Production and Transduction of T Cells

Lentivirus was produced by transiently transfecting HEK293T cells using Lipofectamine 2000 (Invitrogen). Briefly, 9 µg of transfer plasmid, 13.5 µg of LV-MAX lentiviral packaging Mix (Gibco) and 50 ul of lipofectamine 2000 were used for each 100 mm plate seeded 6 million HEK293T cells one day before. Transfection media was replaced with 10 ml OptiMEM in the morning of the next day. Media containing lentivirus was harvested at 48 h post transfection, filtered through 0.45 µm filters, and concentrated by Amicon filter (Sigma) at 4° C. Lentivirus was then frozen at −80° C. Human T cells were transduced 24 h post activation with anti-CD3/CD28 Dynabeads (Invitrogen) by overnight incubation with lentivirus. T cells were transduced once more 16 h after the first transduction. Following transduction, T cells were cultured and expanded for another 8 to 10 days.

Example 5

In Vitro Target Cell Killing Assay $5 \times 10^3$ target cells stably transduced to express GFP and firefly luciferase were co-cultured with either non-transduced or EpCAM targeting CAR T cells at varying effector to target ratios (E:T). Co-cultures were carried out in T cell culture medium containing 150 µg/ml D-Luciferin (Gold Biotechnology) and no cytokine supplementation. Luminescence was measured using a plate reader (BioTek) with readings in each E:T condition normalized to target only controls.

Real Time Cell Analyzer (ACEA Bio) was used to measure killing of primary epithelial cells by CAR T variants. $5 \times 10^3$ target cells were co-cultured with either non-transduced or EpCAM targeting CAR T cells. Co-cultures were carried out in T cell culture medium without cytokine supplementation.

Example 6

EpCAM Binding and CAR Expression Quantification

CAR expression on HEK293T cells was detected using anti-c-myc-FITC (Miltenyi) at the recommended concentration. EpCAM binding to HEK293T cells expressing CAR was detected using recombinant EpCAM (R&D systems) at 360 nM. Recombinant EpCAM was previously conjugated with AF647 using Alexa Fluor 647 Microscale Protein Labeling Kit (Invitrogen). Cells were then washed and resuspended prior to flow cytometry analysis.

Example 7

In Vitro Measurement of IFN-γ and IL-2

Supernatant from E:T assays were collected at 24 hrs and frozen at −80° C. ELISA MAX Deluxe kits (Biolegend) were used to determine IFN-γ and IL-2 levels in supernatants. Cytokine levels were quantitated by following manuals from Biolegend.

Results

Example 8

Identification of a Key Residue in EpCAM Targeting CAR for Affinity Tuning

UBS-54 scFv was designed based on the $V_H$ and $V_L$ sequences of UBS-54 huMab (U.S. Pat. No. 7,777,010B2), which were connected by a linker (SEQ ID NO: 22)

The CDR-H3 sequence of UBS-54 scFv is DPFLHY. To test which amino acid residue was important for the affinity, 4 residues were changed individually to alanine (A) to generate 4 different variants: D1A, F3A, L4A and Y6A (FIG. 1A).

The scFv sequences were synthesized and cloned to generate $2^{nd}$ generation CAR constructs in a lentiviral backbone (FIG. 1B).

Figure 1C:
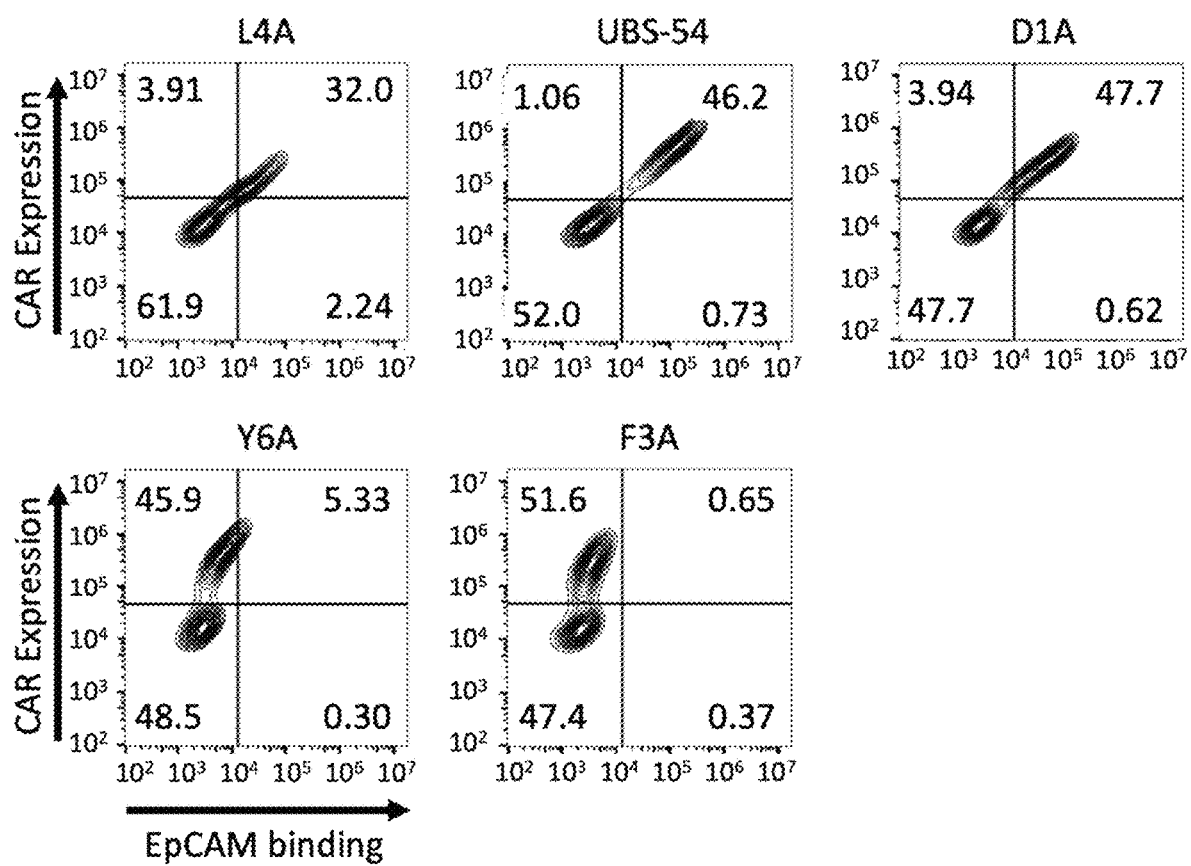
FIG. 1C shows the recombinant EpCAM binding to MYC-tagged CARs expressed in HEK293T cells. X axis: binding of Alexa Fluor 647 labeled recombinant EpCAM. Y axis: binding of anti-MYC antibody.

To test whether alanine substitution changes the affinity of UBS-54 scFv, HEK293T transfected with plasmids encoding CARs containing UBS-54, D1A, F3A, L4A or Y6A scFv, and assayed for EpCAM antigen binding by flow cytometer (FIG. 1C). A myc tag was appended to the N-terminus of each scFv variant to aid measurement of CAR expression by anti-myc-FITC antibody. Recombinant EpCAM protein was previously conjugated with Alexa Fluor 647 (AF647). Higher value of mean fluorescence intensity (MFI) indicated better binding of the myc antibody or EpCAM antigen. The relative affinity of each CAR was estimated using the ratio of AF647 signal intensity to FITC signal intensity ($MFI_{AF647}/MFI_{FITC}$) from cells expressing the CAR. scFv variants were ranked in order of the highest to the lowest (FIG. 1C): L4A($MFI_{AF47}/MFI_{FITC}=$ 0.302)>UBS-54 ($MFI_{AF647}/MFI_{FITC}=0.289$)>D1A ($MFI_{AF647}/MFI_{FITC}=0.246$)>Y6A($MFI_{AF647}/MFI_{FITC}=$ 0.018)>F3A($MFI_{AF647}/MFI_{FITC}=0.016$).

L4A had higher or similar affinity to that of UBS-54. It is a useful antibody, but it is not suitable to be used as an affinity-tuned antibody to lower the cytotoxicity of CAR against normal tissue.

F3A had too low affinity and specificity by a soluble antigen binding assay, and thus is not useful. Further functional analyses on D1A and Y6A CARs were performed as they had a lower affinity than that of UBS-54 CAR but still had a sufficient affinity to bind to EpCAM antigen.

Figures 1D, 2A:
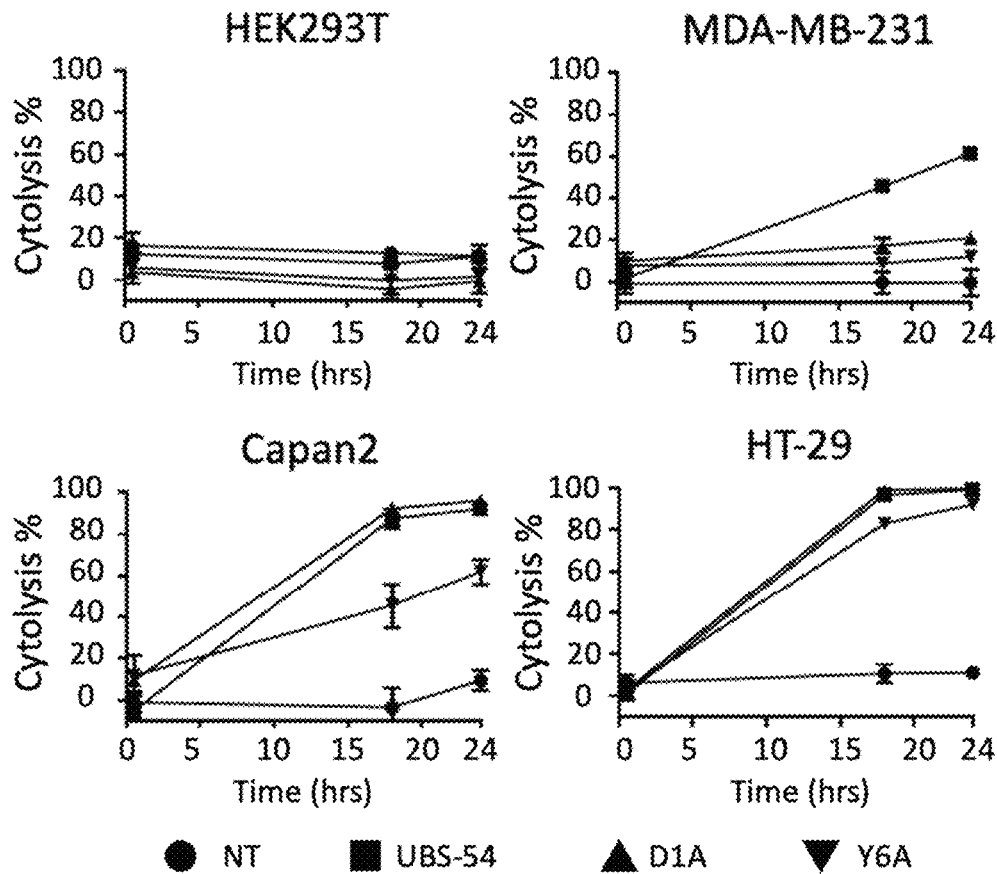
FIG. 1D shows effector to target (E:T) assays for measuring target killing by primary T cells transduced with different EpCAM targeting CARs. Each target was separately incubated with different CAR T cells or non-transduced T (NT) cells at 2.5:1 E:T ratio. Percent of viability was normalized to luminescence from target cell only.
FIG. 2A shows the design of amino acid substitutions in UBS-54 CDR-H3 to fine tune the affinity of EpCAM targeting CARs.

We then examined the influence of lower affinity EpCAM targeting CAR on primary T cell activation and cytotoxicity in vitro. Primary T cells were transduced with UBS-54, D1A and Y6A CARs, and added to various target cells to determine their cytotoxic efficacy in vitro. Overall, there was a positive correlation between the rate of target cell lysis and EpCAM expression (HT-29>Capan2>MDA-MB-231>HEK293T) across all CART cells (FIG. 1D). The rate of killing was also faster when T cells expressed CARs possessing higher affinity for EpCAM (UBS-54>D1A>Y6A).

Example 9

Figure 2B:
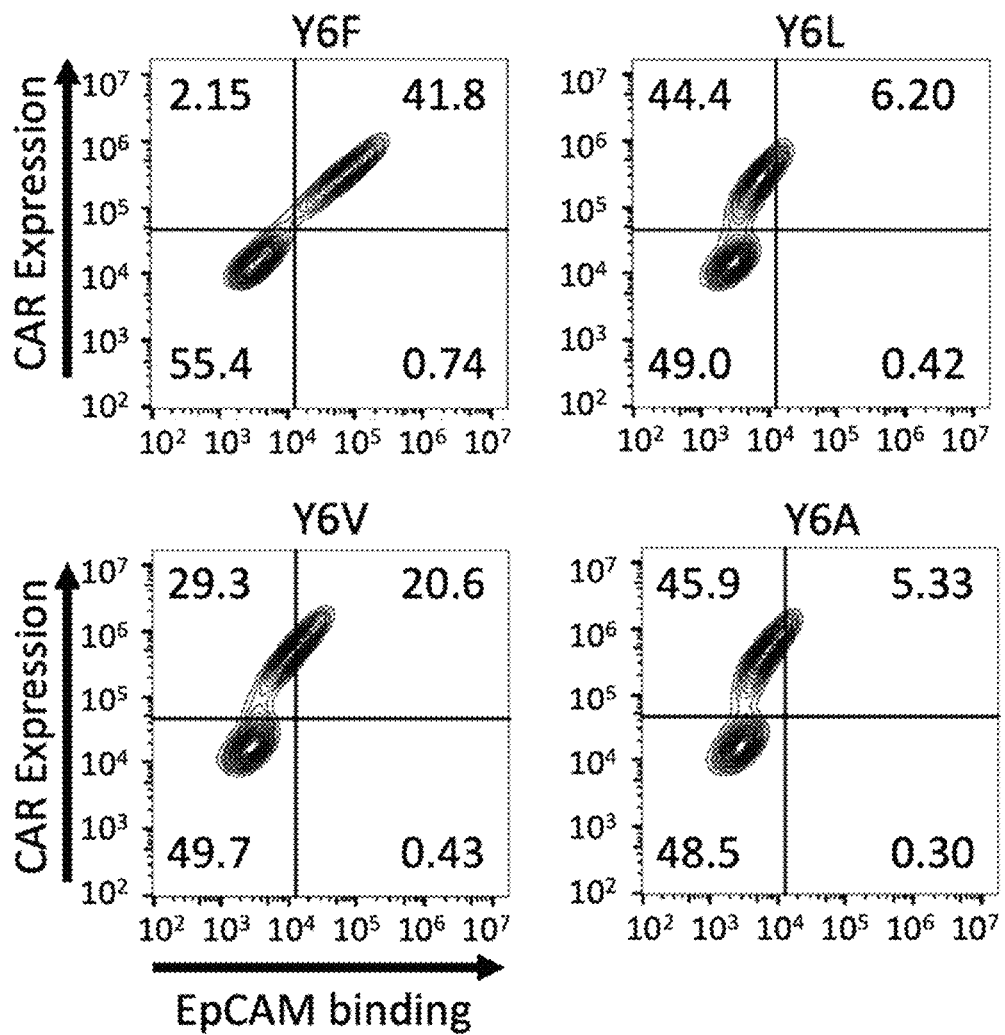
FIG. 2B shows the recombinant EpCAM binding to MYC-tagged CARs expressed in HEK293T cells. X axis: binding of Alexa Fluor 647 labeled recombinant EpCAM. Y axis: binding of anti-MYC antibody

Amino Acid Substitution on the Y6 Residue for Fine Affinity Tuning of EpCAM Targeting CAR To identify CAR variants that could have the affinity in between D1A and Y6A, we generated 3 additional variants (Y6V, Y6L and Y6F) by changing the tyrosine (Y) residue of CDR-H3 to residues with hydrophobic side chains in different size (FIG. 2A). The relative affinity of these CAR variants was measured again (FIG. 2B) by EpCAM binding as described in Example 6. Based on the ratio of $MFI_{AF}647/MFI_{FITC}$, we ranked the affinity of CAR variants in the order of the highest to lowest: UBS-54($MFI_{AF647}/MFI_{FITC}=0.289$)>Y6F ($MFI_{AF647}/MFI_{FITC}=0.239$)>Y6L($MFI_{AF647}/MFIF_{FITC}=0.031$)>Y6V($MFI_{AF647}/MFI_{FITC}=0.026$)>Y6A ($MFI_{AF647}/MFI_{FITC}=0.018$).

Figure 2C:
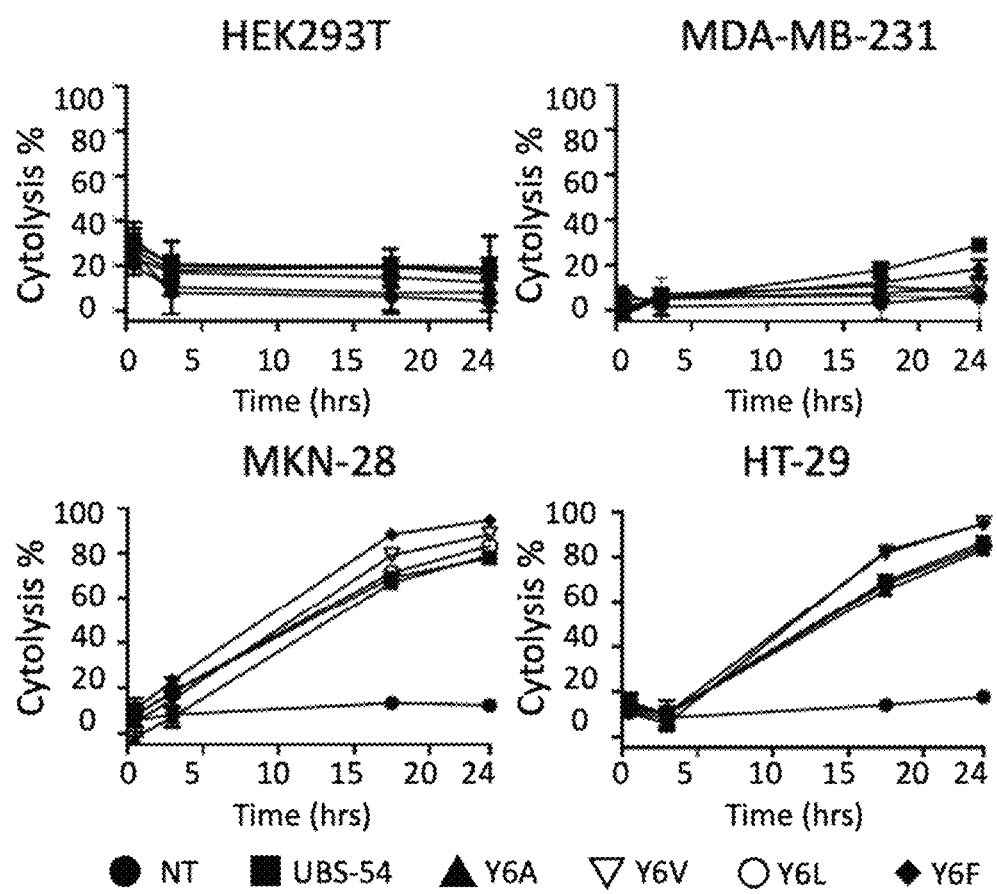
FIG. 2C shows the effector to target (E:T) assay for measuring target killing by primary T cells transduced with different EpCAM targeting CARs. Each target was separately incubated with different CAR T cells or non-transduced T (NT) cells at 1:1 E:T ratio. Percent of cytolysis was normalized to luminescence from target cell only.

We then examined the influence of lower affinity EpCAM targeting CARs on primary T cell activation and cytotoxicity in vitro. Primary T cells were transduced with UBS-54, Y6F, Y6L, Y6V and Y6A CARs, and added to various target cells to determine their cytotoxic efficacy in vitro. All of these CAR T killed EpCAM high cancer cells (HT-29 and MKN-28) (FIG. 2C).

Example 10

Figure 2D:
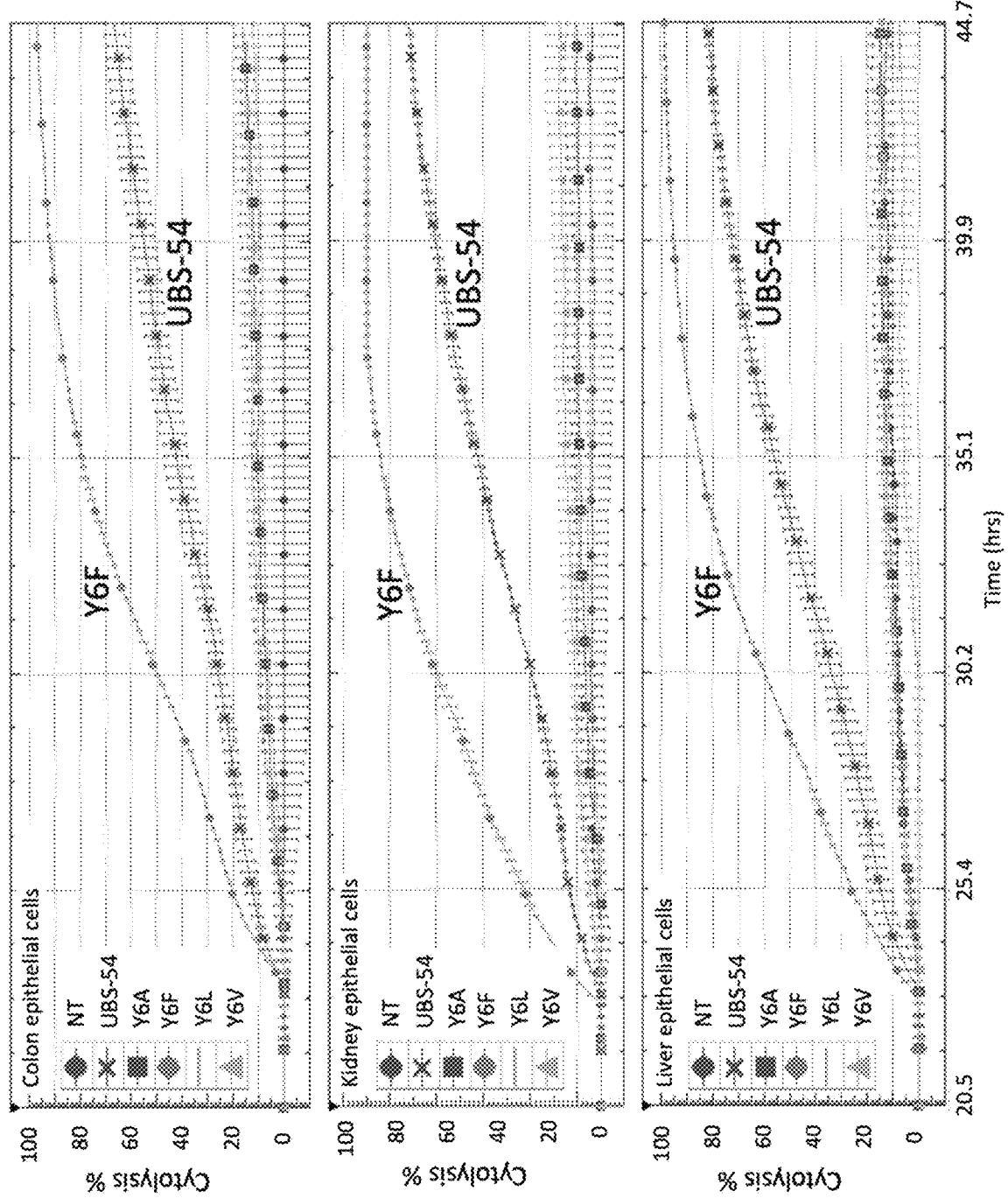
FIG. 2D uses Real Time Cell Analyzer (RTCA) to measure primary epithelial cells killing by EpCAM targeting CAR T. Each primary epithelial cell target was separately incubated with CAR T or NT cells at 1:1 E:T ratio. Percent of cytolysis was normalized to target cell only. X axis: Time, Y axis: percent of cytolysis

Low Affinity CAR T Cells Spared Normal Primary Epithelial Cells in Cytotoxicity Assay Epithelial cell adhesion molecule (EpCAM) is highly expressed in epithelial cells and overexpressed in tumor cells in a variety of epithelial carcinomas. We sought to mitigate the on-target/off-tumor cytotoxicity of CAR T cells by fine affinity tuning. We examined the cytotoxicity of EpCAM targeting CAR T variants to normal primary epithelial cells. Real Time Cell Analyzer (RTCA) allowed us to monitor cell viability in a label-free and real-time manner. EpCAM targeting CAR T cells were added to three primary epithelial cell targets. High affinity UBS-54 and Y6F CAR T cells killed primary epithelial cells (FIG. 2D). Low affinity Y6A, Y6L and Y6V CAR T cells did not killed primary epithelial cells (FIG. 2D), though they all killed EpCAM high cancer cells efficiently as mentioned previously (FIG. 2C).

Figure 2E:
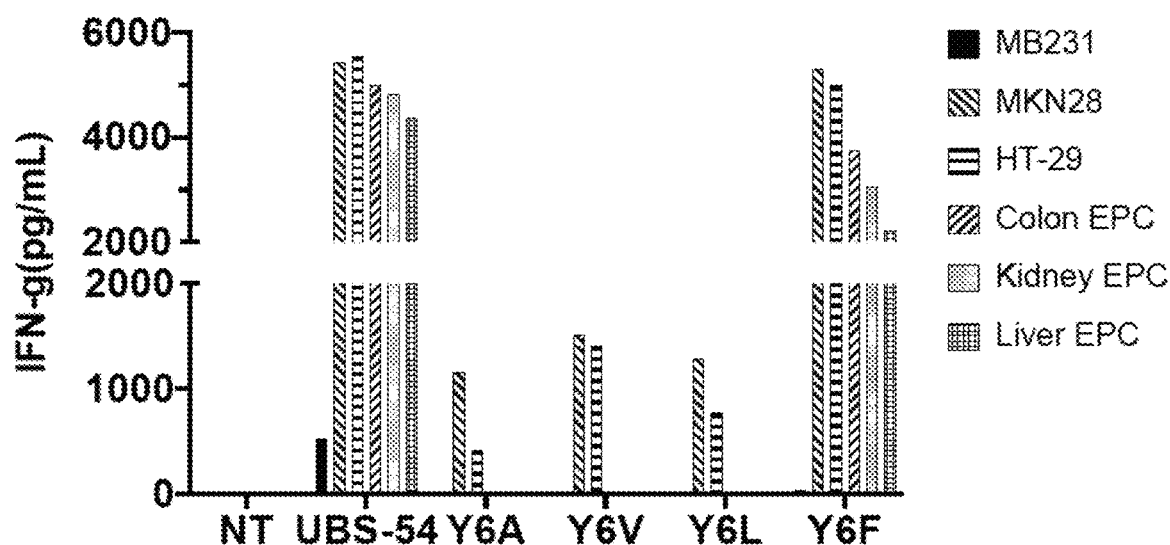
FIG. 2E shows the IFN-γ release measured by ELISA for each CAR T variant after co-incubation with different target cells for 24 hours at E:T=1:1.
Figure 2F:
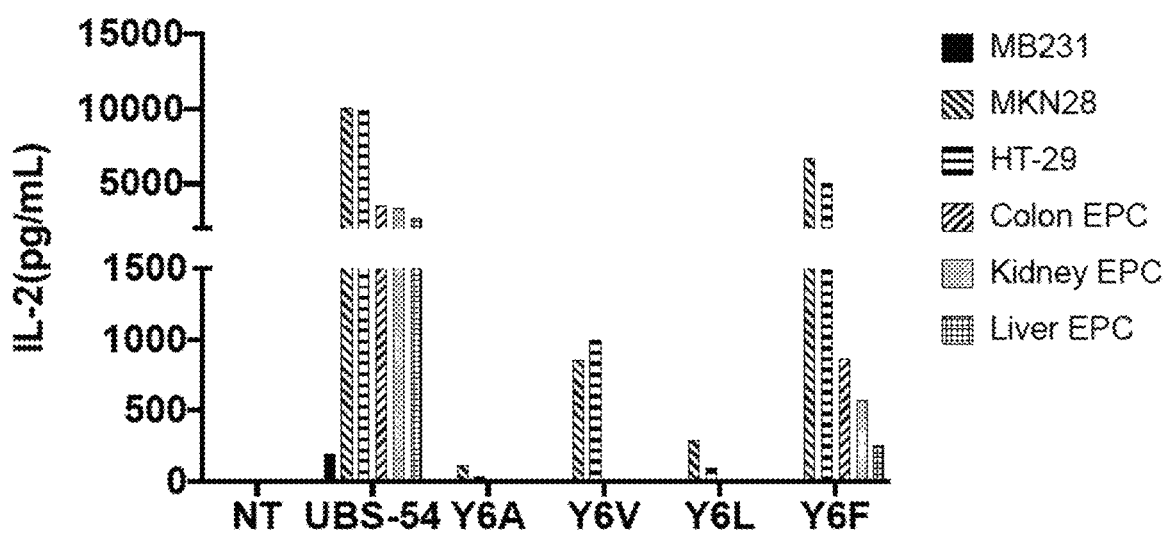
FIG. 2F shows the IL-2 release measured by ELISA for each CAR T variant after co-incubation with different target cells for 24 hours at E:T=1:1.

IFN-γ release (FIG. 2E) and IL-2 release (FIG. 2F) by CAR T cells aligned closely with the affinity of CAR and target antigen density, where increasing levels were found in co-cultures containing higher affinity CAR T cells and target cells with higher EpCAM level. Consistent with the observation that Y6A, Y6L and Y6L did not kill primary epithelial cells, the release of IFN-γ and IL-2 was also at level comparable to those from non-transduced T cells.

These results indicated that we identified three (Y6A, Y6L and Y6V) EpCAM targeting CAR T variants minimally reactive toward normal primary epithelial cells while effectively eliminating cancer cells in vitro.

Example 11

Preclinical Studies to Examine Affinity-Tuned EpCAM CAR T Activity

Intraperitoneal Gastric Cancer Model in Mice
4- to 6-week-old male NSG mice are purchased from the Jackson Laboratory. Peritoneal gastric cancer models are established by injecting $0.5 \times 10^6$ firefly luciferase (FLuc)-expressing SNU-638 gastric cancer cell lines into the peritoneal cavity. After 7 days, non-transduced control T cells NT and anti-EpCAM CAR T cells of the present invention ($10 \times 10^6$/mouse) are injected intraperitoneally.
Systemic Gastric Cancer Model
Gastric cancer cell line MKN-45-FLuc$^+$ tumor cells ($0.5 \times 10^6$/mouse) and T cells ($10 \times 10^6$/mouse) are injected via tail vein. T cells are administered 5 days after tumor inoculation.
Orthotopic Cancer Modelsp
Orthotopic xenograft of human tumors are established by surgical implantation of cancer cell line to stomach at a density of $0.1 \times 10^6$ cells in 25 μL of 1:1 mixture of McCoy's 5A and Matrigel (Corning). Fifteen days later, T cells are injected intravenously via tail vein ($10 \times 10^6$/mouse).
Patient-Derived Xenograft (PDX) Models
No more than 3 passages in mice are used. Seven days after inoculation of tumors, mice are treated with $10 \times 10^6$ T cells via tail vein. Tumor volume (V) is measure with a caliper on a weekly basis, and calculated using the formula $V=[length \times (width)^2]/2$.
Subcutaneous Tumor Model
To mimic heterogenous antigen expression, a mixture of SNU-638 (90% wild-type, 10% EpCAM knockout) or MKN-45 (90% wild-type, 10% EpCAM knockout) tumor cells ($1 \times 10^6$/mouse) are implanted subcutaneously into the upper left flank of NSG mice. Five or seven days later, mice are treated with $10 \times 10^6$ various T cells via intravenous injection. Mouse plasma is harvested and stored at $-80°$ C. for cytokine analysis. Tumors are collected at the indicated time points to measure EpCAM and ICAM-1 expression by flow cytometry.
Monitoring of Tumor Growth, Killing, and CAR T Cell Distribution
All T cells are cryopreserved and used for injection freshly after thawing. Tumor growth is monitored weekly using an IVIS® Spectrum in vivo imaging system (PerkinElmer). Bioluminescence images are acquired 15 minutes after intraperitoneal injection of 200 μL of 15 mg/mL D-luciferin (GoldBio). For peritoneal SNU-638 tumor model, D-luciferin is injected subcutaneously. Whole-body bioluminescence flux is used to estimate tumor burden. PET/CT imaging is performed to track T cell biodistribution using a micro-PET/CT scanner (Inveon, Siemens) 2 hours after intravenous injection of $^{18}$F-NOTA-OCT tracer (1,4,7-Triazaclononane-1,4,7-triacetic acid-octreotide).

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. An antibody or an antigen-binding fragment thereof that binds to Ep-CAM comprising a light chain variable region (VL) and a heavy chain variable region (VH), wherein the VL CDR1, CDR2, and CDR3 have the amino acid sequences of SEQ ID NOs: 12, 13, and 14, respectively; the VH CDR1 and CDR2 have the amino acid sequences of SEQ ID NOs: 10 and 11, respectively; and the VH CDR3 region has the amino acid sequence of SEQ ID NO: 6, 7, 8, 3, 5, or 9.

2. The antibody or the antigen-binding fragment thereof of claim 1, wherein VL comprises the amino acid sequence of SEQ ID NO: 15 or 16, and VH comprises the amino acid sequence of SEQ ID NO: 17, 18, 19, 20, 21, or 22.

3. The antigen-binding fragment of claim 1, which is single chain variable fragment (scFv).

4. The scFv of claim 3, wherein the heavy chain variable CDR3 has the amino acid sequence of SEQ ID NO: 6, 7, or 8.

5. A chimeric antigen receptor fusion protein (CAR) comprising from N-terminus to C-terminus:

(i) a scFv comprising VL and VH, wherein VL comprises the amino acid sequence of SEQ ID NO: 15 or 16, and VH comprises the amino acid sequence of SEQ ID NO: 17, 18, or 19,
(ii) a hinge domain,
(iii) a transmembrane domain,
(iv) at least one co-stimulatory domains, and
(v) an activating domain.

6. The CAR according to claim 5, wherein the co-stimulatory domain is selected from the group consisting of CD28, 4-1BB, ICOS-1, CD27, OX-40, GITR, and DAP10.

7. The CAR according to claim 5, wherein the activating domain is CD3 zeta.

8. An isolated nucleic acid sequence encoding the CAR of claim 5.

9. T cells or natural killer cells modified to express the CAR of claim 5.

10. An adoptive cell therapy method for treating cancer, comprising the steps of:
administering the CAR-T cells of claim 9 to a subject suffering from cancer, wherein the cancer cells of the subject overexpress EpCAM, and the CAR T cells bind to the cancer cells to kill the cancer cells.

11. The method according to claim 10, wherein the cancer is colon, intestine, breast, lung, prostate, gastric, pancreas, bladder, gall bladder, nasopharyngeal, colorectal, ovarian, or lung cancer.

12. The antibody or an antigen-binding fragment thereof according to claim 1, wherein the heavy chain variable CDR3 has the amino acid sequence of SEQ ID NO: 9.

13. The antibody or an antigen-binding fragment thereof according to claim 1, wherein the heavy chain variable CDR3 has the amino acid sequence of SEQ ID NO: 3 or 5.

* * * * *